United States Patent [19]
Douglas

[11] Patent Number: 5,444,670
[45] Date of Patent: Aug. 22, 1995

[54] METHOD AND APPARATUS FOR DETERMINING SOIL STRENGTH FROM DOPPLER-SHIFTED ACOUSTIC SIGNATURES

[75] Inventor: Bretton L. Douglas, Santa Barbara, Calif.

[73] Assignee: Sonatech, Inc., Santa Barbara, Calif.

[21] Appl. No.: 303,051

[22] Filed: Sep. 8, 1994

[51] Int. Cl.$^6$ .......................... G01V 1/38; G01N 3/30
[52] U.S. Cl. .......................... 367/90; 73/594; 73/170.32; 73/84
[58] Field of Search ............ 73/81, 84, 594, 170.32; 367/13, 38, 90, 21

[56] References Cited

U.S. PATENT DOCUMENTS

| | | | |
|---|---|---|---|
| 4,007,633 | 2/1977 | Thompson | 73/84 |
| 4,186,373 | 1/1980 | Thompson | 367/131 |
| 4,382,384 | 5/1983 | Mitchell et al. | 73/594 |

OTHER PUBLICATIONS

Underwater Systems Design, *Developments in Cone Penetration Testing for Site Investigations*, by Dr. C. W. Swain, Fugro Limited, Feb./Mar. 1983.
Sonatech, Inc., Sounder, *Artic Tests Verify Performance of Penetrometer*, vol. 1, No. 1, Summer 1987.
Technical Report, R855, *Expendable Doppler Penetrometer: A Performance Evaluation*, by R. M. Beard, Jul. 1977.
Design News, *Seabed Penetrator Transmits Data by Wireless Signals*, Dec. 3, 1984.
*Sea Bed Surveys by Acoustic Penetrometer*, by Reginald J. Cyr.
Technical Report R905, *Expendable Doppler Penetrometer For Deep Ocean Sediment Strength Measurements*, by R. M. Beard, Mar. 1984.
Technical Report 242, *Interaction of Sound with the Ocean Bottom: A Three-Year Summary*, By H. E. Morris, E. L. Hamilton, H. P. Bucker, R. T. Bachman, Apr. 1978.

*Primary Examiner*—Ian J. Lobo
*Attorney, Agent, or Firm*—Nydegger & Associates

[57] ABSTRACT

A signal processing system for determining sea floor composition based on the frequency waveform and Doppler shift transmitted from an acoustic penetrometer includes a hydrophone for receiving the penetrometer waveform. The hydrophone output is digitized and passed to a general purpose computer where it is analyzed by a signal processing program. The signal processing program performs various signal transformations to increase the quality of the input waveform and isolates a penetration event. Additionally, the input signal is converted to an equivalent velocity waveform. A curve fitting algorithm is then used to determine the points within the velocity waveform that mark the initiation and termination of the penetration event that corresponds to the impact of the penetrometer with the sea floor. Once the initiation and termination of the penetration event are known, the velocity waveform is numerically integrated between those two points. The result of the numerical integration calculates the depth of penetration achieved during the penetration event. Based on the depth of penetration and other data, such as size and weight of the penetrometer, the composition of the sea floor at the point of impact may be characterized.

16 Claims, 3 Drawing Sheets

METHOD AND APPARATUS FOR DETERMINING SOIL STRENGTH FROM DOPPLER-SHIFTED ACOUSTIC SIGNATURES

FIELD OF THE INVENTION

The present invention pertains to testing devices which determine the physical characteristics and near surface conditions of ocean floor soil formations. More particularly, the present invention pertains to signal processing systems which determine the physical characteristics of the sea floor by analyzing the Doppler effect, i.e. frequency shift, generated by an acoustic penetrometer as the penetrometer impacts and penetrates into the sea floor. The present invention is particularly, but not exclusively, useful as a means to isolate and analyze the frequency shift associated with the deceleration of a constant frequency acoustic sound source during penetration of the sea floor.

BACKGROUND OF THE INVENTION

Knowledge of the composition and structure of the sea floor in a particular area, or along particular paths on the sea floor, can be extremely valuable information. For instance, knowledge of the soil composition of the sea floor, to include the surface of the sea floor and the upper layer of the sea floor to a depth of approximately three or four feet, can be extremely helpful in selecting sites for underwater structures and determining workable routes for cable and pipe line locations. Historically, penetrometers have long been used to determine the physical characteristics of the sea floor. Early penetrometers were projectile-shaped physical sampling devices which impacted the sea floor, then took a soil sample back to the surface for analysis. More recently, penetrometers have been equipped with instrumentation that measures their velocity and acceleration as they impact the sea floor. In operation, the penetrometer is dropped into the water from a surface vessel or aircraft, and allowed to impact and penetrate the sea floor. As the penetrometer impacts and penetrates the sea floor, data describing its deceleration is recorded. This data is then analyzed to determine the depth of penetration achieved by the penetrometer. In turn, the depth of penetration may be used to generate an accurate characterization of the sea floor at the point of impact.

A number of different penetrometer types have been employed. For example, one type of penetrometer has been adapted to carry an accelerometer and associated recording device. Penetrometers of this type require retrieval prior to analysis of the impact data and retrieval generally necessitates the penetrometer be harnessed during descent. This requirement can effectively limit the accuracy of the information obtained. Furthermore, recovery of this type of penetrometer also involves a significant delay at each drop site. A second type of penetrometer uses fine wires to link an on-board accelerometer to a remote shipboard recorder. For this type penetrometer, retrieval is not required but wire failures have generally limited effectiveness of the design.

A third type of penetrometer relies on the Doppler shift associated with a moving acoustic sound source rather than the response of an accelerometer as described previously. Penetrometers of this third type are generally referred to as acoustic penetrometers. In operation, an acoustic penetrometer carries a fixed frequency acoustic sound source and is dropped into the water from a surface vessel or aircraft. A remote receiver then records the acoustic waveform generated by the acoustic penetrometer as it descends and penetrates the sea floor.

During descent, the acoustic penetrometer undergoes a period of acceleration during which the penetrometer may reach its terminal velocity. In any event, the penetrometer's downward velocity is ended with an abrupt deceleration as the penetrometer impacts and penetrates the sea floor. As the acoustic penetrometer accelerates and decelerates, the acoustic waveform recorded at the remote receiver exhibits a corresponding change in frequency. Specifically, during downward acceleration, the recorded waveform exhibits a gradually decreasing frequency. On the other hand, when the penetrometer impacts the sea floor, the recorded waveform exhibits an abrupt increase in frequency. This effect, caused by the relative motion of the penetrometer with respect to the remote receiver, is known as the Doppler Effect. According to the Doppler Effect, the actual frequency ($f_o$) of the waveform perceived at the remote receiver is related to the true fixed frequency (f) of the acoustic waveform generated by the penetrometer by:

$$f_o = f(v/(v-v_s))$$

where v is the speed of sound in sea water, and $v_s$ is the speed of the descending penetrometer.

The relationship between the frequency ($f_o$) perceived by the remote receiver and the downward velocity of the penetrometer allows the frequency waveform recorded by the remote receiver to be translated into an equivalent velocity waveform. More importantly, the resulting velocity waveform may be further analyzed to determine the distance travelled by the penetrometer during its period of rapid deceleration as it impacts and penetrates the sea floor. In turn, the distance travelled by the penetrometer during the penetration event may be used to generate an accurate characterization of the sea floor at the point of impact.

Various difficulties are, however, inherent in the use of Doppler effect and acoustic penetrometers. As can be readily appreciated, the time between penetrometer release and eventual impact may involve many seconds or minutes. In comparison, the actual penetration event may only last for a fraction of a second. Additionally, the overall frequency shift associated with the descending penetrometer is limited by the eventual speed attained by the penetrometer and is, therefore, modest. As a result, location of the penetration event involves searching a large amount of data and locating the relatively slight frequency shift associated with the penetration event.

Once the penetration event is determined, further difficulties emerge. As previously discussed, the calculation of penetration depth requires that the times associated with the initiation and termination of the penetration event be isolated. Unfortunately, the brief duration and relatively slight frequency shift associated with the penetration event make identification of these two critical times difficult. Identification of the initiation and termination times of the penetration event is further complicated by the inevitable presence of noise in the ocean environment.

A system which analyzes the Doppler effect on the acoustic waveform that results as a penetrometer impacts and penetrates into the sea floor is disclosed in U.S. Pat. No. 4,007,633 which was issued to Thompson for an invention entitled "Method of Determining the Physical Characteristics of a Sea Floor." The Thompson system, however, relies on analog processing of the recorded frequency waveform. As a result, the ability of the Thompson system to first locate and then to analyze the acoustic information associated with the penetration event is limited. In particular, the Thompson system lacks a highly developed ability to identify the initiation and termination of the penetration event.

The present invention recognizes the need for an inexpensive signal processing system which is capable of being used in combination with disposable acoustic penetrometers. In light of the above, it is an object of the present invention to provide a signal processing system that can accurately characterize sea floor composition. Still another object of the present invention is to provide a signal processing system that is relatively immune to acoustic noise. Yet another object of the present invention is to provide a signal processing system that can be used in combination with disposable acoustic penetrometers. It is another object of the present invention to provide a signal processing system that includes an enhanced ability to detect and analyze a penetration event. Still another object of the present invention is to provide a signal processing system that can be used in combination an acoustic penetrometer which is simple to use, relatively easy to manufacture, and comparatively cost effective.

SUMMARY OF THE PREFERRED EMBODIMENTS OF THE INVENTION

The method and apparatus for determining sea floor consistency according to the present invention includes a hydrophone for receiving acoustic signals from a penetrometer which is fitted with a fixed frequency acoustic sound source. In practice, the hydrophone will typically be deployed from a surface ship or helicopter but other applications are equally practical. As the penetrometer descends, the hydrophone receives a characteristic waveform from the acoustic generation on the penetrometer. Most importantly, as the penetrometer decelerates during the penetration event, the waveform received by the hydrophone is marked by a rapid increase in frequency.

Electronic signals from the hydrophone, which correspond to the acoustic signals received by the hydrophone, are initially processed by an amplifier unit. The amplifier unit processes the raw electronic signals from the hydrophone to selectively amplify the frequency region of the signals that corresponds to the waveform generated by the descending acoustic penetrometer. Once processed by the amplifier unit, the amplified and filtered waveform is processed by an analog-to-digital converter and then passed to a general purpose computer.

Once input into the general purpose computer, the digital waveform describing the penetrometer's descent is subject to a series of transformations. As a result of these transformations, the waveform region associated with the penetration event is isolated and data not associated with the penetration event is discarded. Once the data which is not associated with the penetration event has been eliminated, the remaining waveform is digitally filtered to further eliminate noise not associated with the descending acoustic penetrometer. The filtered waveform is converted to a complex-valued signal by Hilbert transformation, and the instantaneous phase of the signal is obtained from the complex-valued signal. The instantaneous phase is differentiated in time to obtain the instantaneous received frequency. The difference between the instantaneous received frequency and the probe frequency is used to estimate the velocity of the probe for each time sample. This velocity estimate has an error term caused by acoustic noise in the receiver. Therefore, the velocity record is smoothed by an adaptive algorithm to provide a velocity estimate with smaller variance.

After the initial transformations, each remaining data sample represents the downward velocity of the acoustic penetrometer at a given point in time. It may be appreciated that the penetrometer velocity waveform generated by this process may be used to calculate the distance travelled by the penetrometer between two points in time. More importantly, if the point where the penetration event begins and the point where the penetration event ends are known, the velocity waveform may be used to calculate the depth of penetration.

In general terms, the initiation and termination points of the penetration event are determined by application of an algorithmic curve fitting process. The curve fitting process of the present invention assumes that, at the point of penetration, the upward forces acting on the penetrometer increase proportionally to $(time)^\alpha$ where $\alpha$ is an empirical constant. Based on that assumption, a generalized set of equations are assumed to describe the velocity of the penetrometer before, during and after the penetration event. The actual times where penetration begins and ends are chosen as the times where the actual waveform most accurately fits the generalized equations.

Based on the penetrometer velocity waveform and the calculated initiation and termination times of penetration, the depth of penetration is calculated by numerically integrating the velocity waveform starting at the point where penetration begins and terminating where the penetration event ends. Once the penetration depth is calculated, information describing the physical characteristics of the penetrometer such as weight and size may be combined with the calculated depth of penetration to determine the soil strength of the sea floor at the point of impact.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF PREFERRED EMBODIMENTS

Figure 1:
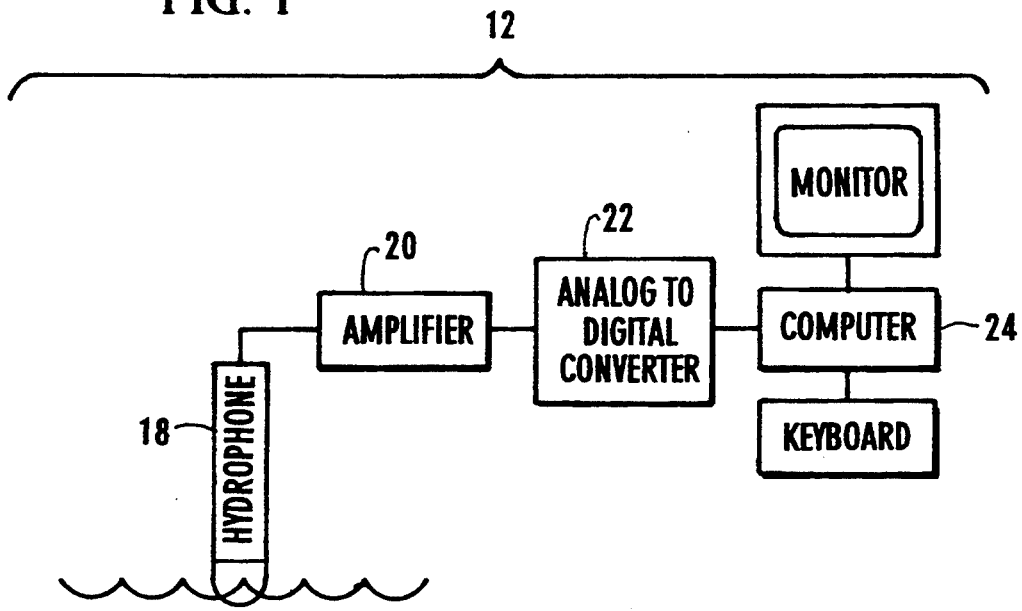
FIG. 1 is a schematic diagram of the signal processing system of the present invention shown with an acoustic penetrometer.
Figure 1:
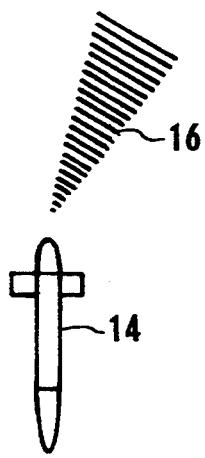

Referring initially to FIG. 1, the signal processing system of the present invention is shown and generally designated 12. As shown in FIG. 1, the signal processing system 12 is designed to work in combination with an acoustic penetrometer 14 which emits a fixed frequency acoustic waveform 16. The signal processing system 12 further includes a hydrophone 18, an amplifier/filter 20, an analog-to-digital converter 22 and a general purpose computer 24 which are interconnected generally as shown in FIG. 1.

Figure 2:
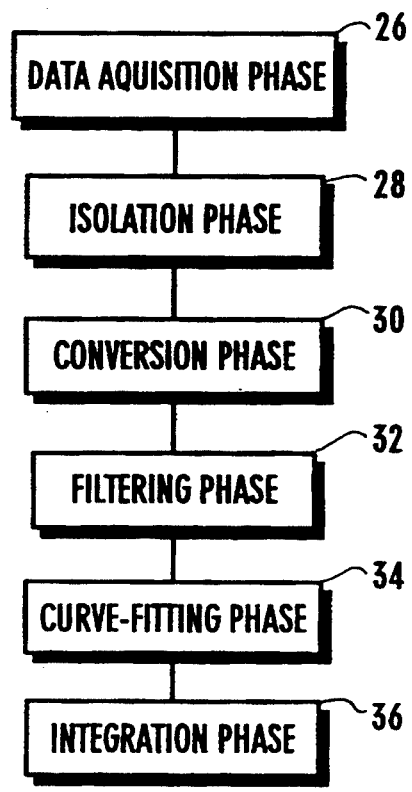
FIG. 2 is a data-flow diagram showing the steps associated with operation of the present invention.

The flow of data through the signal processing system 12 is represented in general form in FIG. 2. As FIG. 2 shows, operation of the signal processing system 12 begins with a data acquisition phase 26. The data acquisition phase 26 is initiated as the penetrometer 14 is released and continues until some time after the penetrometer 14 has impacted the sea floor. During the data acquisition phase 26, the fixed frequency acoustic waveform 16 emitted by the penetrometer 14 is received by the hydrophone 18. The output of the hydrophone 18 is passed to the amplifier/filter 20 where it is conditioned, amplified and filtered prior to being passed to an analog-to-digital converter 22. Once processed by the analog-to-digital converter 22, the waveform, now in digital form, is passed to the general purpose computer 24.

Upon completion of the data acquisition phase 26, it may be appreciated that a digital record 38 of input to the hydrophone 18 has been passed to the general purpose computer 24. It may also be appreciated that the digital waveform 38 consists of numerous data samples where each sample corresponds to the voltage produced by the hydrophone 18 at a particular point in time.

Figure 3:
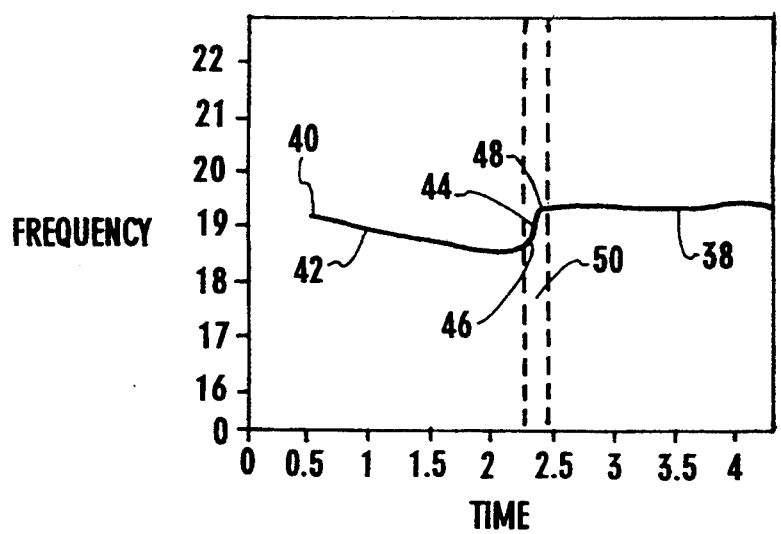
FIG. 3 is a graph showing the frequency of the penetrometer waveform as perceived by the signal processing system of the present invention as a function of time, as an acoustic penetrometer is released, descends and impacts with the sea floor.

As shown in FIG. 3, however, the waveform of the digital record 38 is not a straight line as would be associated with a hydrophone receiving a fixed frequency signal. Instead, the digital record 38 corresponds to the fixed frequency acoustic waveform 16 emitted by the penetrometer 14 as modified by the Doppler shift associated with the velocity of the descending penetrometer 14. Specifically, FIG. 3 shows that the digital record 38 starts at the point designated 40 which corresponds in time to the release of the penetrometer 14. At the point of release, the downward velocity of the penetrometer 14 is relatively small. As a result, the digital record 38 at point 40 substantially matches the fixed frequency acoustic waveform 16 emitted by the penetrometer 14.

As the penetrometer 14 accelerates, however, the frequency received by the hydrophone 18 exhibits a corresponding decrease. Point 42 of the digital record 38, therefore, exhibits a decreased voltage level corresponding in comparison with point 40. The penetrometer 14 rapidly approaches a terminal velocity, so that the velocity of the penetrometer 14 relative to the hydrophone 18 is substantially constant after about 2 seconds. As a result, the digital record 38 is substantially constant prior to the impact of the penetrometer 14 with the sea floor. The impact of the penetrometer 14, known as the penetration event 44, is characterized by an abrupt increase in the frequency received by the hydrophone 18. In FIG. 3, it can be seen that the abrupt increase in frequency associated with the penetration event 44 results in an upward shift in the digital record 38 that begins at the point 46. The upward shift in the digital record 38 that begins at point 46 ends at point 48. It may be appreciated that point 48 represents the end of the penetration event 44 and indicates that the penetrometer 14 has come to rest.

For the purposes of the present invention, only the portion of the digital record 38 associated with the penetration event 44 is useful. Therefore, as indicated in FIG. 2, the data acquisition phase 26, is followed by an isolation phase 28. In general terms, the isolation phase 28 seeks to isolate and extract the region of digital record 38, known at the penetration event window 50, associated with the penetration event 44. The extraction of the penetration event window 50 is accomplished by performing a binary search of the digital record 38. To perform the binary search, the digital record 38 is divided into two distinct regions. One of the two regions is then tested to determine whether it contains the penetration event 44. The binary search process continues with the region that is determined to contain the penetration event 44. The binary search terminates when the digital record 38 can no longer be subdivided without subdividing the penetration event 44. For purposes of illustration, the penetration event window 50 associated with the region of the digital record 38 corresponding to the penetration event 44 is shown in FIG. 3 and designated 50. The effect of the isolation phase 28 may also be seen by comparing FIG. 3 where the penetration event window 50 occupies a small portion of the total graph to FIGS. 4 through 8 where the penetration event window 50 has been magnified to occupy the entire graph.

Figure 4:
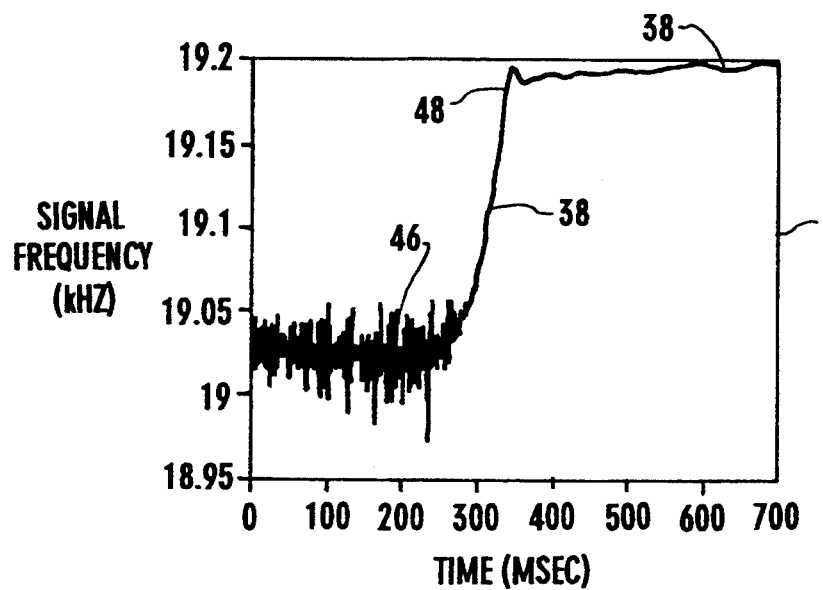
FIG. 4 is a graph, expanded in time, showing the frequency of the perceived penetrometer waveform after isolation of the penetration event and application of various signal processing transformations.
Figure 5:
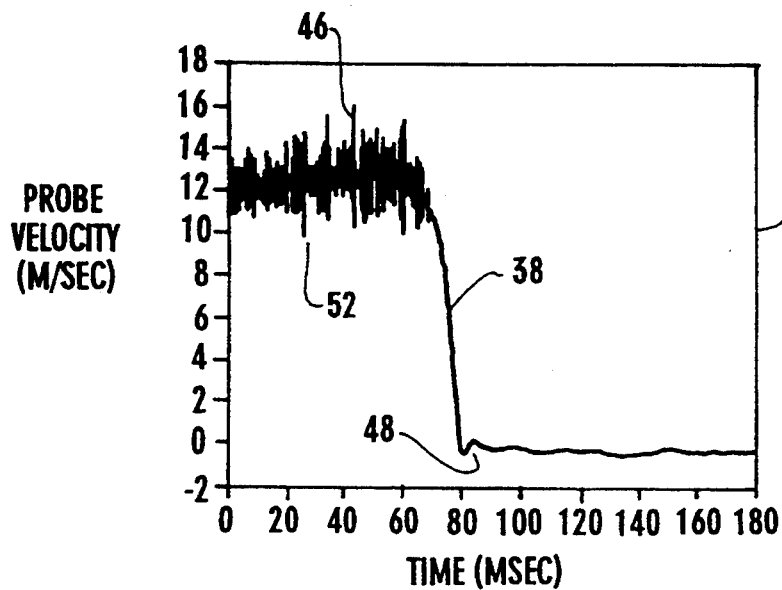
FIG. 5 is a graph showing an equivalent velocity waveform calculated from the perceived penetrometer waveform shown in FIG. 4.

At the completion of the isolation phase 28, only the portion of the digital record 38 contained in the penetration event window 50 remains eligible for further processing. As shown in FIG. 2, the remaining data now enters the conversion phase 30. The conversion phase 30 generally applies a series of signal processing transformations designed to enhance the portion of the digital record 38 actually associated with the fixed frequency acoustic waveform 16 emitted by the penetrometer 14. Concurrently, extraneous noise present in the digital record 38 is attenuated. Most importantly, during the conversion phase 30, each voltage sample in the digital record 38 is converted into a complex-valued signal through Hilbert transformation. The instantaneous phase of the complex valued signal is then calculated and differentiated to obtain an instantaneous frequency value which corresponds to the original voltage sample. Each frequency value is then converted to an equivalent velocity sample by application of the following formula:

$$\text{velocity} = v * (f - \text{sample frequency})/f$$

where v represents the speed of sound in sea water and f is the fixed acoustic frequency 16 emitted by the penetrometer 14. FIG. 4 shows the penetration event window 50 before processing by the conversion phase 30. In comparison, FIG. 5 shows the penetration event window 50 after the conversion phase 30 has translated the voltage samples in the digital record 38 to equivalent velocity samples.

Figure 6:
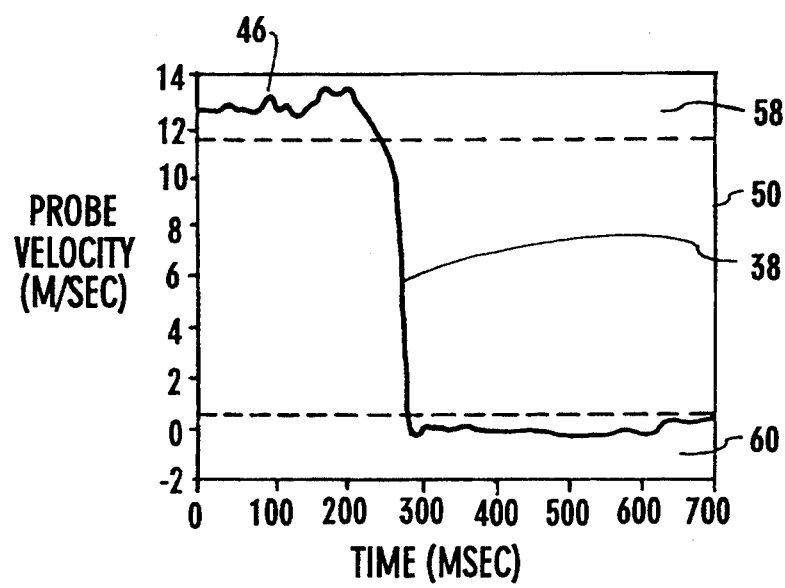
FIG. 6 is a graph depicting the equivalent velocity waveform shown in the last figure after application of a noise reduction algorithm.

Once the digital record 38 has been converted to velocity data, the smoothing phase 32 is entered. At the input to the smoothing phase 32, the digital record 38 within the penetration event window 50 contains a relatively large amount of noise caused by ambient sea noise and interference resulting from the fixed frequency acoustic waveform 16 emitted by the penetrometer 14 echoing in the marine environment. Noise of this type is shown in FIGS. 4 and 5 and designated 52. In particular, it can be seen that the noise 52 effectively obscures the point 46 of the digital record 38 that corresponds to the beginning of the Doppler shift associated with the penetration event 50. Therefore, the smoothing phase 32 applies a series of transformations which attenuate the noise in the penetration event window 50. The effects of these transformations are seen in FIG. 6 where it can be seen that point 46 is no longer effectively obscured by noise.

Following the data flow diagram of FIG. 2, it can be seen that the smoothing phase 32 is followed by a curve-fitting phase 34. It may be appreciated that at the initiation of the curve-fitting phase 34, each data sample within the penetration event window 50 describes the velocity of the penetrometer 14 at some point in time. The curve-fitting phase 34, locates in the penetration event window 50, the initiation of the penetration event 54 and the termination of the penetration event 56.

To simplify the data processing task associated with locating the initiation of the penetration event 54 and the termination of the penetration event 56, the curve-fitting phase 34 first selects two regions within the penetration event window 50. The first region 58 is limited the portion of the penetration event window 50 where the velocity samples exceed eighty percent of the maximum velocity attained by the penetrometer 14 during descent. In a similar fashion, the second region 60 is limited to the portion of the penetration event window 50 where the velocity samples are less than twenty percent of the maximum velocity attained by the penetrometer 14 during descent. Selection of the first region 58 and the second region 60 is illustrated in FIG. 6.

Once the first region 58 and the second region 60 have been selected, the two regions of the penetration event window 50 are analyzed in terms of an empirical model. The model assumes that during the beginning of the penetration event 44, the upward forces acting on the penetrometer 14 increase proportionally to $(time)^\alpha$ where $\alpha$ is an empirical constant. Based on that assumption, a generalized set of equations are assumed to describe the velocity of the penetrometer 14 before, during and after the penetration event 44. The actual initiation of the penetration event 54 is chosen as the time where the digital record 38 within the first region 58 of the penetration event window 50 most accurately fits the generalized equations. Specifically, The initiation of the penetration event 54 ($t_o$) is located by assuming that prior to the penetration event 44, the velocity of the penetrometer 14 may be represented by a first equation 62:

$$\text{velocity} = v_0 + a_0 t \text{ (for } t < t_o)$$

and that once the penetration event 44 has started, the velocity of the penetrometer 14 may be represented by a second equation 64:

$$\text{velocity} = v_0 + a_0 t - b_0 (t - t_o)^{\alpha + 1} \text{ (for } t > t_o)$$

Figure 7:
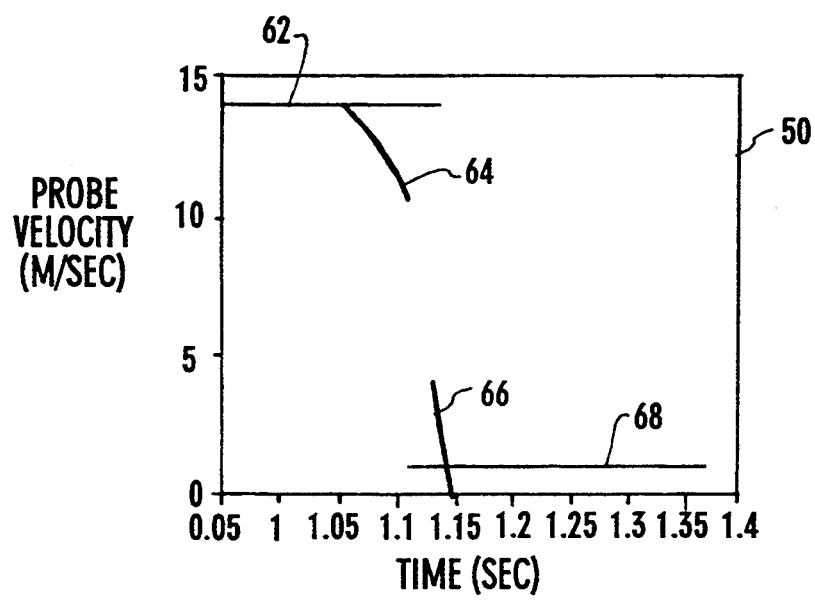
FIG. 7 is a graph showing the four equations used to approximate the initiation and termination of the penetration event.
Figure 8:
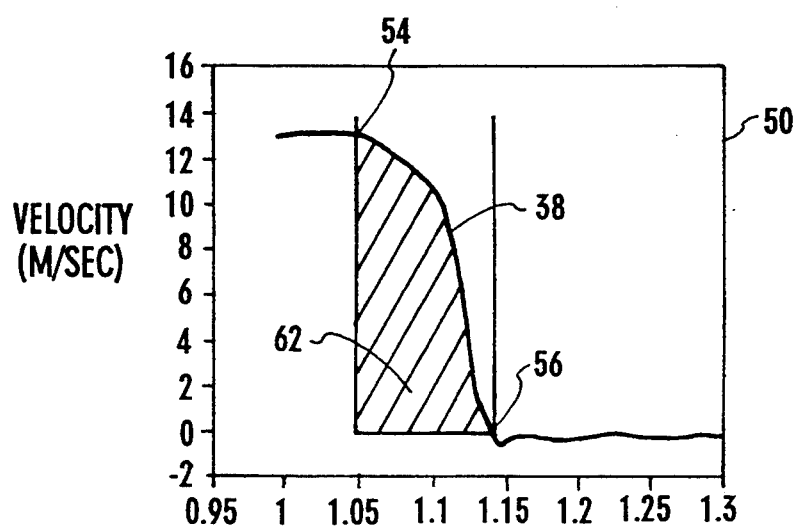
FIG. 8 is a graph showing the filtered velocity waveform and the area of numerical integration bounded by the initiation of a penetration event and the termination of a penetration event.

Using these two equations, each possible $t_o$ in the first region 58 is examined and optimal $v_o$, $a_o$ and $b_o$ values are selected. The $t_o$ that best fits the two equations is selected as the actual $t_o$ or the initiation of the penetration event 54. Use of the curve-fitting process may be best appreciated by reference to FIGS. 7 and 8. In FIG. 7, it can be seen that a line representing the first equation is shown and designated 62. FIG. 7 also shows a curve corresponding to the second equation designated 64. It may be appreciated that the combination of the line defined by the first equation 62 and the curve defined by the second equation 64 may be used to approximate the region of the digital record 38 that contains the initiation of the penetration event 54. The value of $t_o$ that results in the best curve fit defines the initiation of the penetration event 54 as shown in FIG. 8.

In a similar fashion, time $t_1$, the termination of the penetration event 56, is extracted from the second region 60 of the penetration event window 50. In this case, the termination of the penetration event ($t_i$) is located by assuming that prior to the penetration event 44, the velocity of the penetrometer 14 may be represented by a third equation 66:

$$\text{velocity} = v_1 + a_1 t \text{ (for } t < t_1)$$

and that once the penetration event 44 has ended, the velocity of the penetrometer 14 may be represented by a forth equation 68:

$$\text{velocity} = v_2 + a_2 t \text{ (for } t > t_1)$$

Using these two equations, each possible $t_1$ in the second region 60 of the penetration event window 50 is examined and optimal $v_1$, $v_2$, $a_1$ and $a_2$ values are selected. The $t_1$ that best fits the two equations is selected as the actual $t_1$ or the termination of the penetration event 56. It can be seen by reference to FIGS. 7 and 8 that the third equation 66 as well as the forth equation 68 may be represented by lines designated 66 and 68 respectively. More specifically, it can be seen that the termination of the penetration event 56 may be approximated by the intersection of the lines defined by equation 66 and equation 68. The approximation that results in the best curve fit defines the termination of the penetration event 56 as shown in FIG. 8.

At the completion of the curve-fitting phase 34, the velocity data in the digital record 38 is subject to a final transformation designed to remove the effects of wave motion as well as the motion of the vehicle carrying the signal processing system 12. In more detail, each data sample in the digital record is corrected by application of the following equation:

$$\text{corrected velocity} = \text{sample velocity} - (v_2 + a_2 t)$$

where $v_2$ and $a_2$ are the same values previously calculated.

As shown in FIG. 2, the final phase in the data flow diagram is the integration phase 36. At the beginning of the integration phase 36, the initiation of the penetration event 54 and the termination of the penetration event 56 are known. In addition, the digital record 38 within the penetration event window 50, describes the speed of the penetrometer 14 between the initiation of the penetration event 54 and the termination of the penetration event 56. Based on this data, the depth of penetration is calculated by numerically integrating the digital record 38 starting at the initiation of the penetration event 54 and ending at termination of the penetration event 56. The numerical integration calculates the area under the curve represented by the digital record 38 and corresponds to the depth of penetration achieved by the penetrometer 14. The process of numerical integration is shown in greater detail in FIG. 8 where it can be seen that the initiation of the penetration event 54 and the termination of the penetration event 56 define a bounded region of the digital record 38. It may also be seen that the result of the numerical integration calculates the area 62 under the curve defined by the digital record 38 and bounded by the initiation of the penetration event 54 and ending at termination of the penetration event 56.

Once the penetration depth is calculated, information describing the physical characteristics of the penetrometer 14 such as weight and size may be combined with the calculated depth of penetration to determine the composition of the sea floor at the point of impact.

While the particular Method and Apparatus for Determining Material Consistency from Impact Deceleration Data as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A method for determining the compaction and shear strength of sea soil which comprises the steps of:
   launching a penetrometer from a vehicle into the sea;
   recording reception data of a fixed frequency waveform transmitted from an acoustic sound source mounted on said penetrometer;
   locating a frequency shift in said receptions during a penetration event, said penetration event occurring during a time interval measured from a time before said penetrometer impacts the sea floor and a time after said penetrometer comes to rest on the sea floor;
   converting said frequency shift into a velocity shift;
   smoothing said velocity shift to minimize the effects of extraneous acoustic noise;
   fitting said velocity shift with a first algorithm to determine a first time, said first time approximating initiation of said penetration event;
   fitting said velocity shift with a second algorithm to determine a second time, said second time approximating termination of said penetration event; and
   using said first time, said second time, and said velocity shift to establish penetration depth of said penetrometer for determining the compaction and shear strength of the sea soil.

2. A method as recited in claim 1 wherein the step of locating a frequency shift further comprises the steps of:
   establishing a time lapse;
   dividing said time lapse into a first sector and a second sector;
   finding said frequency shift in either said first sector or said second sector to establish a new time lapse with said frequency shift therein; and
   repeating said dividing and finding steps as desired to establish said time interval.

3. A method as recited in claim 2 wherein said time interval is approximately one and one half seconds (1.5 sec).

4. A method as recited in claim 1 wherein said converting step further comprises the steps of:
   filtering said reception data to improve the signal to noise ratio; and
   refining said filtered reception data with a Hilbert Transformation process to recover said frequency shift therefrom.

5. A method as recited in claim 1 further comprising the step of smoothing said velocity shift.

6. A method as recited in claim 5 further comprising the steps of:
   choosing a nominal time window;
   smoothing said velocity shift with said nominal time window;
   determining an estimated standard deviation for said velocity shift after said smoothing step;
   dividing said estimated standard deviation by a reference standard deviation to obtain a new time window; and
   smoothing said velocity shift with said new time window.

7. A method as recited in claim 1 wherein said first algorithm establishes said first time ($t_o$) when $t_o$ best fits the relationships $$v_i = v_o + a_o t;\text{ and}$$

$$v_p = v_o + a_o t - b_o (t - t_o)^{\alpha + 1}$$

where:
$\alpha$ is an empirically determined constant,
$v_i$ is the measured velocity of said penetrometer before the initiation of said penetration event,
$v_o$ is the best fit parameter for velocity before the initiation of said penetration event,
$a_o$ is the best fit parameter for acceleration before the initiation of said penetration event,
$v_p$ is the measured velocity of said penetrometer after the initiation of said penetration event, and
$b_o$ is the best fit parameter for acceleration after the initiation of said penetration event.

8. A method as recited in claim 7 wherein said second algorithm establishes said second time ($t_1$) when $t_1$ best fits the relationships $$v_i = v_1 + a_1 (t - t_1);\text{ and}$$

$$v_f = v_2 + a_2 t$$

where:
$v_i$ is the measured velocity of said penetrometer before the end of said penetration event,
$v_1$ is the best fit parameter for velocity of said penetrometer before the end of said penetration event,
$a_1$ is the best fit parameter for acceleration of said penetrometer before the end of said penetration event,
$v_f$ is the measured velocity of said penetrometer after the end of said penetration event, $v_2$ is the best fit parameter for velocity of said penetrometer after the end of said penetration event, and $a_2$ is the best fit parameter for acceleration of said penetrometer after the end of said penetration event.

9. A method as recited in claim 1 further comprising the step of correcting said velocity shift to compensate for movement of the vehicle.

10. A system for determining the compaction and shear strength of sea soil which includes:

means for launching a penetrometer from a vehicle into the sea, said penetrometer emitting a fixed frequency acoustic waveform;

means for recording frequency data, said frequency data consisting of said acoustic waveform as received at said vehicle;

means for converting said frequency data to equivalent velocity data;

means for determining a first time, said first time being defined as the time when said penetrometer begins to impact the sea floor;

means for determining a second time, said second time being defined as the time when said penetrometer comes to rest on said sea floor;

means for calculating the penetration depth of said penetrometer using said velocity data, said first time and said second time; and means for converting said penetration depth, weight of said penetrometer and configuration of said penetrometer into average shear strength in cohesive soils, and compaction in noncohesive soils.

11. A system as recited in claim 10 wherein the means for determining said first time ($t_o$) chooses $t_o$ when $t_o$ best fits the relationships:

$$v_i = v_o + a_o t; \text{ and}$$

$$v_p = v_o + a_o t - b_o (t - t_o)^{\alpha+1}$$

where:

$\alpha$ is an empirically determined constant, $v_i$ is the measured velocity of said penetrometer before said penetrometer begins to impact said sea floor, $v_o$ is the best fit parameter for velocity before said penetrometer begins to impact said sea floor, $a_o$ is the best fit parameter for acceleration before said penetrometer begins to impact said sea floor, $v_p$ is the measured velocity of said penetrometer after said penetrometer begins to impact said sea floor, and $b_o$ is the best fit parameter for acceleration after said penetrometer begins to impact said sea floor.

12. A system as recited in claim 10 wherein the means for determining said second time ($t_1$) chooses $t_1$ when $t_1$ best fits the relationships:

$$v_i = v_1 + a_1 (t - t_1); \text{ and}$$

$$v_f = v_2 + a_2 t$$

where:

$v_i$ is the measured velocity of said penetrometer after said penetrometer impacts said sea floor and before said penetrometer comes to rest on said sea floor, $v_1$ is the best fit parameter for velocity of said penetrometer after said penetrometer impacts said sea floor and before said penetrometer comes to rest on said sea floor, $a_1$ is the best fit parameter for acceleration of said penetrometer after said penetrometer impacts said sea floor and before said penetrometer comes to rest on said sea floor, $v_f$ is the measured velocity of said penetrometer after said penetrometer comes to rest on said sea floor, $v_2$ is the best fit parameter for velocity of said penetrometer after said penetrometer comes to rest on said sea floor, and $a_2$ is the best fit parameter for acceleration of said penetrometer after said penetrometer comes to rest on said sea floor.

13. A system as recited in claim 10 wherein the means for calculating the penetration depth of said penetrometer includes the steps of numerically integrating said velocity data bounded by said first time and said second time.

14. A system for determining penetration depth from the frequency waveform generated by an acoustic penetrometer as the penetrometer impacts the sea floor which includes the steps of:

digitizing said frequency waveform;

converting said digitized frequency waveform to a velocity waveform;

locating a penetration event within said velocity waveform;

locating a first time ($t_o$) within said velocity waveform, said first time ($t_o$) approximating the initiation of said penetration event using a first algorithm;

locating a second time ($t_1$) within said velocity waveform, said second time approximating the termination of said penetration event using a second algorithm; and numerically integrating said penetrometer velocity data between said first time and said second time to calculate the depth of penetration of said penetrometer.

15. A system as recited in claim 14 wherein said first algorithm establishes said first time ($t_o$) when $t_o$ best fits the relationships:

$$v_i = v_o + a_o t; \text{ and}$$

$$v_p = v_o + a_o t - b_o (t - t_o)^{\alpha+1}$$

where:

$\alpha$ is an empirically determined constant, $v_i$ is the measured velocity of said penetrometer before the initiation of said penetration event, $v_o$ is the best fit parameter for velocity before the initiation of said penetration event, $a_o$ is the best fit parameter for acceleration before the initiation of said penetration event, $v_p$ is the measured velocity of said penetrometer after the initiation of said penetration event, and $b_o$ is the best fit parameter for acceleration after the initiation of said penetration event.

16. A system as recited in claim 14 wherein said second algorithm establishes said second time ($t_1$) when $t_1$ best fits the relationships:

$$v_i = v_1 + a_1 (t - t_1); \text{ and}$$

$$v_f = v_2 + a_2 t$$

where:

$v_i$ is the measured velocity of said penetrometer before the end of said penetration event, $v_1$ is the best fit parameter for velocity of said penetrometer before the end of said penetration event, $a_1$ is the best fit parameter for acceleration of said penetrometer before the end of said penetration event, $v_f$ is the measured velocity of said penetrometer after the end of said penetration event, $v_2$ is the best fit parameter for velocity of said penetrometer after the end of said penetration event, and $a_2$ is the best fit parameter for acceleration of said penetrometer after the end of said penetration event.

* * * * *